United States Patent
Vaultier et al.

(10) Patent No.: US 7,179,940 B2
(45) Date of Patent: Feb. 20, 2007

(54) (ARYL)(AMINO) BORANE COMPOUNDS, METHOD FOR PREPARING SAME

(75) Inventors: Michel Vaultier, Châteaugiron (FR); Gilles Alcaraz, Rennes (FR); Christophe Duriez, Maurecourt (FR); Lisenn Euzenat, Rennes (FR); Yann Ribourdouille, Chalon sur Saone (FR)

(73) Assignees: Centre National de la Recherche Scientifique, Paris (FR); Universite de Rennes, Rennes (FR)

( * ) Notice: Subject to any disclaimer, the term of this patent is extended or adjusted under 35 U.S.C. 154(b) by 54 days.

(21) Appl. No.: 10/499,728

(22) PCT Filed: Dec. 20, 2002

(86) PCT No.: PCT/FR02/04512

§ 371 (c)(1),
(2), (4) Date: Jan. 3, 2005

(87) PCT Pub. No.: WO03/053981

PCT Pub. Date: Jul. 3, 2003

(65) Prior Publication Data

US 2005/0107633 A1    May 19, 2005

(30) Foreign Application Priority Data

Dec. 21, 2001  (FR) .................................. 01/16734

(51) Int. Cl.
*C07F 5/02*       (2006.01)
(52) U.S. Cl. ........................................................ 564/9
(58) Field of Classification Search .................. 564/9
See application file for complete search history.

(56) References Cited

FOREIGN PATENT DOCUMENTS

JP          54-83435 A       7/1979

OTHER PUBLICATIONS

Mayer et al., Contributions to the chemistry of boron. 203. Reactions of some nonmetallic elements with 9-fluorenylidene(2,2,6,6-tetramethylpiperidino)borane, Chemische Berichte (1990), 123(5), 963-6.*

Mikhailov et al., Organiboron Compounds, Synthesis and Transformation of Complex Compounds of Arylboranes and secondary amines, Izvestiya Adademii Nauk, SSSR, Seriya, 1962, 1213-18.*

Burg et al., Dimethylaminomethylborine, Journal of the American Chemical Society (1956), 78, 1521-2.*

Noeth et al., Chemistry of boron. XXI. The symmetrical dialkylbis-(dimethylamino)diborons Zeitschrift fuer Anorganische und Allgemeine Chemie (1963), 324(3-4), 129-45.*

Kraemer et al., "Synthese und Struktur von 1,2-Bis(diIsopropylamino)-1,2-diboretan Synthesis and Structure of 1,2-Bis(diisopropylamino)-1,2-diboretane"; XP001105324, vol. 45b, pp. 1019-1021, Jul. 1990.

Koester et al., Cyclisierungen von Bor-Stickstoff-Verbindungen in der Hitze, Justus Liebigs Annalen Der Chemie, Verlag Chemie GmbH, Weinheim, DE, XP-001097997, vol. 720, pp. 23-31, 1968.

Kraemer et al., "Synthese und Strucktur eines 1,2,5,6-Tetrahydro-1,2,5,6-tetraborocins", Angewandte Chemie, International edition, XP001105025, vol. 100, No. 7, p. 963, 1988.

Ishiyama et al., "Paliadium (O)-Catalyzed Cross-Coupling Reaction of Alkoxydiboron with Haloarenes: A direct Procedure for Arylboronic Esters"; Journal of Organic Chemistry, American Chemical Society, XP000863639, pp. 7508-7510, 1995.

Murata et al., "Palladium(O)-Catalyzed Coupling Reaction of Dialkoxyborane with Aryl Halides: Convenient Synthetic Route to Arylboronates"; Journal of Organic Chemistry, American Chemical Society, XP001135064, vol. 62, No. 19, pp. 6458-6459, 1997.

Search Report issued in International Application No. PCT/FR02/04512, Apr. 10, 2003.

* cited by examiner

*Primary Examiner*—Thurman K. Page
*Assistant Examiner*—Chukwuma Nwaonicha
(74) *Attorney, Agent, or Firm*—Buchanan Ingersoll & Rooney PC

(57) ABSTRACT

The invention concerns (aryl)(amino)borane compounds and a method for preparing same. Said compounds are of formula A-BH—$NR^1R^2$, wherein: $R^1$ and $R^2$ are selected among linear, branched or cyclic alkyl radicals, and arylalkyl radicals, or $R^1$ and $R^2$ form together an alkylene; and A represents an aromatic or heteroaromatic group optionally polycondensed, or a group selected among the vinyl, dienyl, polyenyl and alkynyl groups, all said groups optionally bearing at least one substituent. The compounds are obtained by a method which consists in preparing an amine-borane $R_1R^2NH.BH_3$ complex, in transforming it into aminoborane $R^1R^2NBH_2$ by heating, then in reacting it with an A-X compound wherein X is a leaving group.

25 Claims, No Drawings

(ARYL)(AMINO) BORANE COMPOUNDS, METHOD FOR PREPARING SAME

CROSS-REFERENCE TO RELATED APPLICATIONS

This application is a §371 application of International Patent Application No. PCT/FR02/04512, filed Dec. 20, 2002, and published in French on Jul. 3, 2003, as International Publication No. WO 03/053981 A1, which claims priority to French Patent Application No. 01/16734, filed Dec. 21, 2001. The disclosures of these applications are incorporated herein in their entirety.

BACKGROUND OF THE INVENTION

1. Field of the Invention

The present invention relates to (aryl) (amino)borane compounds and to a process for their preparation.

2. Description of the Related Art

Arylboronic acids and esters are generally prepared by borylation of aromatic organomagnesium or organolithium derivatives. These methods are expensive, require specific conditions and are not general, which renders them rather unattractive. They have also been prepared by reaction of tetraalkoxydiboron compounds with brominated or iodinated aromatic derivatives in the presence of palladium catalysts (T. Ishiyama et al., J. Org. Chem., 1995, 60, 7508). This method does not involve organomagnesium or organolithium compounds but the preparation of the tetraalkoxydiboron compounds requires the use of molten metallic sodium or potassium at high temperature in highly flammable solvents, which renders the method dangerous. Pinacolborane can react with brominated or iodinated aromatic derivatives in the presence of palladium catalysts to give arylboronic esters of pinacol (M. Murata et al., J. Org. Chem., 1997, 62, 6458). However, pinacolborane, prepared from the borane-dimethyl sulfide complex ($Me_2S.BH_3$), is a volatile product used in excess and is not very reactive. The boronic esters obtained are very stable and do not make possible ready refunctionalization around the boron atom.

SUMMARY OF THE INVENTION

The aim of the present invention is to provide boranes which can be used in particular in a coupling reaction, that is to say a reaction for the borylation of various derivatives, which can be prepared by a simple process, which exhibit sufficient stability to be stored and which can be readily refunctionalized. For this reason, the subject matter of the present invention is aminoborane compounds and a process for preparing them.

DETAILED DESCRIPTION OF THE PREFERRED EMBODIMENTS

The compounds of the present invention correspond to the formula A—BH—$NR^1R^2$, in which:

$R^1$ and $R^2$ are identical or different groups chosen from linear alkyl groups, branched alkyl groups, cyclic alkyl groups or arylalkyl groups, or else the $R^1$ and $R^2$ groups together form an alkylene group, and A represents:
  a) an optionally polycondensed aromatic group optionally carrying at least one substituent,
  b) an optionally polycondensed heteroaromatic group optionally carrying at least one substituent,
  c) a group chosen from vinyl, dienyl, polyenyl or alkynyl groups optionally carrying at least one substituent, said optional substituents of the groups defined in a), b) and c) being chosen from alkyls, alkoxys, aminos, dialkylaminos, halogens, nitrile groups, ester groups, amide groups, aldehyde groups protected in the acetal or thioacetal form, ketone groups protected in the acetal or thioacetal form, trialkylsilyl groups and dialkoxyboryl groups.

When an $R^1$ or $R^2$ substituent is an alkyl group, it is preferably chosen from linear alkyls having from 2 to 20 carbon atoms, branched alkyls having from 3 to 20 carbon atoms or cycloalkyls having from 3 to 20 carbon atoms. Mention may be made, by way of example, of isopropyl, cyclohexyl or α-methylbenzyl. The $R^1$ and $R^2$ substituents can be chiral groups.

When an $R^1$ or $R^2$ substituent is chosen from arylalkyl groups, it can be an $R^8$-Ph-CH($R^3$) group in which Ph represents a phenyl group, $R^8$ represents H or a substituent chosen from halogens, alkyls, alkoxys, alkylthios, ketone groups protected in the acetal or thioacetal form, and trialkylsilyl groups, and $R^3$ is an alkyl group having from 1 to 20 carbon atoms. Methylbenzyl is particularly preferred.

When $R^1$ and $R^2$ form an alkylene group, the alkylene group is preferably a —$CR^4R^5$—$(CH_2)_n$—$CR^6R^7$— group in which $3 \leq n \leq 5$ and the $R^4$ to $R^7$ substituents are chosen, independently of one another, from H and alkyl radicals having from 1 to 20 carbon atoms. 1,1,5,5-Tetramethylpentylene is a particularly preferred biradical.

Mention may in particular be made, as examples of substituent A, of phenyl, tolyl and methoxyphenyl.

The compounds of the present invention can be prepared by a two-stage process, in which:

During the first stage, an amine-borane complex $R^1R^2NH.BH_3$ is prepared and is then converted to aminoborane $R^1R^2NBH_2$ by heating.

During the second stage, the aminoborane $R^1R^2NBH_2$ is reacted with a compound A-X, in which X is a leaving group, in the presence of a catalytic amount of a complex of a transition metal and of a base, in an aprotic organic solvent or an amine, and then the excess reactants and solvent are removed. The solvent preferably has a boiling point between 50° C. and 250° C. The leaving group X can be, for example, a halogen atom or a triflate, tosylate, mesylate, diazonium or phosphate group.

In a first embodiment, to prepare the amine-borane complex during the first stage, an amine $R^1R^2NH$ is reacted under an inert atmosphere with a borane source in a polar aprotic solvent at a temperature of less than 50° C. and then the solvent is removed under vacuum. The borane source can be a commercial complex, such as $Me_2S.BH_3$ or $THF.BH_3$. The duration of the reaction is at least equal to 2 hours. The polar aprotic solvent used in this stage is preferably chosen from ethers. Mention may in particular be made of THF, dioxane, DME or diglyme, and tert-butyl methyl ether (TBDME).

In a second embodiment, the amine-borane complex can be prepared during the first stage by reaction of the hydrochloride of the amine $R^1R^2NH.HCl$ with $NaBH_4$ or $KBH_4$ in an appropriate solvent, such as THF or an ether/water mixture, according to a process described by Polivka et al. (Coll. Czech. Chem. Commun., 1969, 34, 3009). The amine-borane complex $R^1R^2NH.BH_3$ is subsequently isolated by filtration and removal of the solvent under vacuum.

In both cases, the aminoborane $R^1R^2NBH_2$ is subsequently obtained by heating the amine-borane complex, followed by distillation. Heating is carried out at a temperature which depends on the nature of the $R^1$ and $R^2$ groups. It is 130° C. for $R^1=R^2=$isopropyl. The pure aminoborane obtained after distillation can be stored under an inert atmosphere of nitrogen or of argon.

The organic solvent of the second stage is preferably chosen from ethers, amines and aromatic hydrocarbons. Mention may in particular be made of dioxane, THF, toluene and xylene.

The base introduced into the reaction medium during the second stage of the process is chosen from cyclic or linear trialkylamines, cyclic or linear secondary amines, or aromatic amines of the pyridine or quinoline type.

The complex of a transition metal is preferably a palladium compound stabilized by a ligand. The palladium compound can be chosen from $PdCl_2$, palladium diacetylacetonate $Pd(acac)_2$, palladium acetate $Pd(OAc)_2$, palladium cyanide $Pd(CN)_2$ or allylpalladium chloride $(CH_2=CHCH_2PdCl)_2$. The ligand can be a phosphine, for example chosen from triphenylphosphine $PPh_3$ or sodium triphenylphosphinetrisulfonate TPPTS. In addition, the ligand can be an arsine, such as, for example, triphenylarsine, an aromatic or nonaromatic nitrile, for example chosen from acetonitrile or benzonitrile, an isonitrile, for example chosen from methyl isonitrile or tert-butyl isonitrile, an aromatic or heteroaromatic imine, such as, for example, N-methylbenzylimine, or an imidazo-2-ylidene, such as, for example, N,N'-dibenzylimidazo-2-ylidene.

A compound according to the present invention can be used as reactant for various reactions and in particular for Suzuki-Miyaura couplings.

A few specific reactions are illustrated below by way of examples by a reaction scheme given in each of the cases for an aminoborane compound in which $R^1=R^2=iPr$ and A is a phenyl group carrying a Z substituent. Of course, similar reactions can be carried out using aminoborane compounds obtained from amines other than diisopropylamine.

The reaction of a compound according to the invention with a diethanolamine makes it possible to obtain an arylboratrane, according to the following reaction scheme:

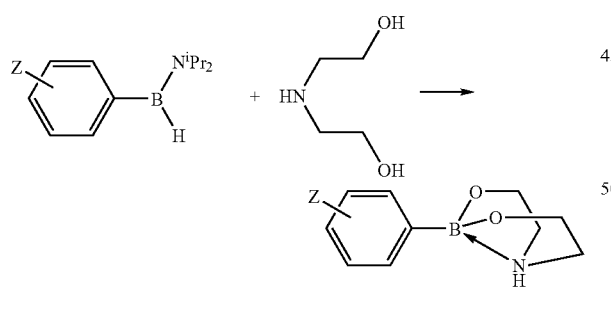

The reaction of a compound according to the invention with 2,2-dimethylpropane-1,4-diol makes it possible to obtain a 2-aryl-5,5-dimethyl-1,3,2-dioxaborinane, according to the following reaction scheme:

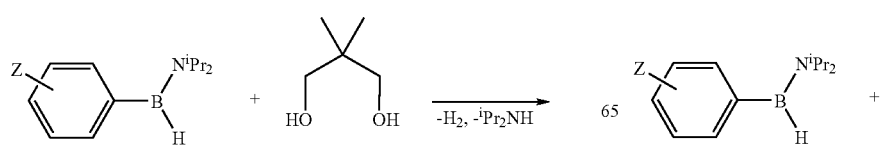

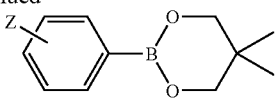

The reaction of a compound according to the invention with excess methanol makes it possible to obtain an aryldimethoxyborane which can subsequently be hydrolyzed to arylboronic acid, according to the following reaction scheme:

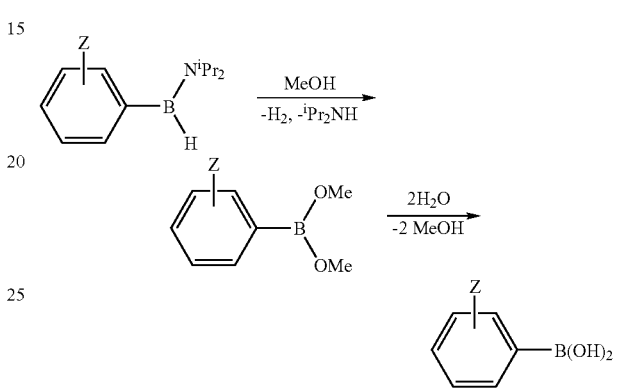

The reaction of a compound according to the invention with a compound A-X in the presence of a Pd(0) catalyst and of a base makes it possible to obtain a (B,B-diaryl)aminoborane compound, according to the following reaction scheme:

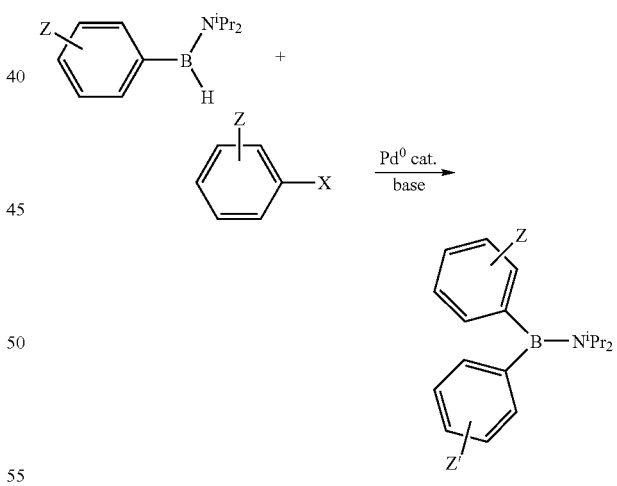

The reaction of a compound according to the invention with a compound A-Z in the presence of a Pd(0) catalyst, of a base and of water makes it possible to obtain a compound Ar—Ar, according to the following reaction scheme:

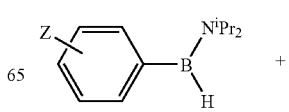

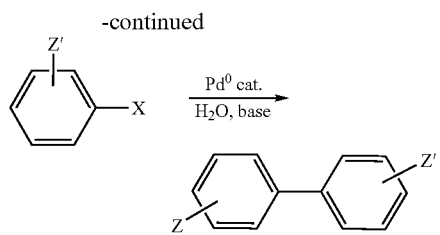

The present invention is described below in more detail with the help of examples, to which it is, however, not limited.

EXAMPLE 1

(p-tolyl)(diisopropylamino)borane

Preparation of the diisopropylamine-borane Complex

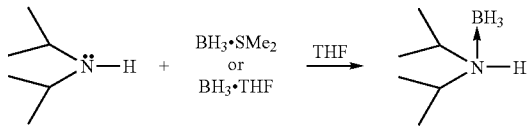

50 ml (357 mmol) of diisopropylamine, freshly distilled over calcium hydride, and 50 ml of anhydrous THF are introduced with stirring into a 250 ml Schlenk vessel dried beforehand under argon. The reaction mixture is cooled to −78° C. using an ethanol/liquid nitrogen cold bath and 36.5 ml of the commercial 9.77 m $BH_3 \cdot SMe_2$ complex (357 mmol) are added dropwise. The temperature of the reaction medium is allowed to rise to ambient temperature over 2 h. The THF is subsequently evaporated on a vane pump under a vacuum of 0.01 mmHg and 41 g of the diisopropylamine-borane complex are obtained in the form of a liquid with syrupy consistency. The spectroscopic characteristics of the compound are given below.

| | |
|---|---|
| $^1$H NMR(CDCl$_3$, δ ppm/TMS): | 1.25(q, 3H, $^1J_{BH}$=97Hz, B$\underline{H}_3$) |
| | 1.26(d, 6H, $^3J_{HH}$=2.6Hz, C$\underline{H}_3$) |
| | 1.29(d, 6H, $^3J_{HH}$=2.6Hz, C$\underline{H}_3$) |
| | 3.10(d hept, 2H, $^3J_{HH}$=2.6Hz, C$\underline{H}$) |
| | 3.45(m, 1H, N$\underline{H}$) |
| $^{11}$B NMR(CDCl$_3$, δ ppm/Et$_2$O.BF$_3$): | −21.4(q, $^1J_{BH}$=97Hz, $\underline{B}H_3$) |
| $^{13}$C NMR(CDCl$_3$, δ ppm/TMS): | 19.4(s, 2C, $\underline{C}H_3$) |
| | 21.4(s, 2C, $\underline{C}H_3$) |
| | 52.5(s, 2C, $\underline{C}H$) |
| Mass spectrometry: | calculated for $[C_6H_{17}N^{11}B]^{\cdot+}$: 114.1454 |
| | found(e.i.): 114.1432(19 ppm) |

Preparation of diisopropylaminoborane:

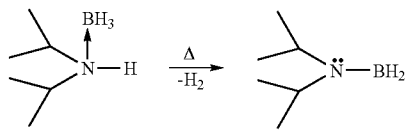

A 250 ml Schlenk vessel, containing 41 g (356.5 mmol) of the pure diisopropylamine-borane complex and surmounted by a distillation column equipped with a ground-glass thermometer and connected to a round-bottomed receiving flask and to a bubbler, is brought, using a sand bath, to 160° C. (temperature of the sand). Steady evolution of dihydrogen occurs and is maintained during the rise in temperature. The distillation temperature of the diisopropylaminoborane at the column top is 91–93° C. The diisopropylaminoborane distills in the form of a colorless liquid. 36 g (318.5 mmol) of compound are recovered, corresponding to a yield of 89%.

Spectroscopic Characteristics:

| | |
|---|---|
| $^1$H NMR(CDCl$_3$, δ ppm/TMS): | 1.3(d, 12H, $^3J_{HH}$=6.7Hz, C$\underline{H}_3$) |
| | 3.4(hept, 2H, $^3J_{HH}$=6.7Hz, C$\underline{H}$) |
| | 5.0(q, 2H, $^1J_{BH}$=125.9Hz, B$\underline{H}_2$) |
| $^{11}$B NMR(CDCl$_3$, δ ppm/Et$_2$O.BF$_3$): | 35.4(t, $^1J_{BH}$=126Hz, $\underline{B}H_2$) |
| $^{13}$C NMR(CDCl$_3$, δ ppm/TMS): | 23.8(s, 4C, $\underline{C}H_3$) |
| | 51.1(s, 2C, $\underline{C}H$) |
| Infrared: | 2488 and 2460 cm$^{-1}$($ν_{BH}$) |
| Mass spectrometry: | calculated for $[C_6H_{16}N^{11}B]^{\cdot+}$: 113.1376 |
| | found(e.i.): 113.1371(4 ppm) |

Preparation of (p-tolyl) (diisopropylamino)borane 0.343 g (0.49 mmol) of palladium catalyst $(Ph_3P)_2PdCl_2$, 2.129 g (9.8 mmol) of p-iodotoluene, 6.8 ml (49 mmol) of triethylamine, 30 ml of dioxane and 3 ml (19.5 mmol) of diisopropylaminoborane were introduced into a 250 ml Schlenk vessel dried beforehand under argon. The Schlenk vessel was subsequently equipped with a reflux condenser connected at the top to a bubbler. The reaction mixture was stirred magnetically and heated at 70° C. for 15 h. The reaction mixture was subsequently allowed to return, under argon, to ambient temperature. The solvent and the excess reactants were evaporated under the vacuum of a vane pump. The residue obtained was taken up in anhydrous ether and then filtered under argon through dry Celite® 545. The filtrate was again evaporated and the residue was distilled in a Kügelrohr distillation apparatus (T=30–35° C.) under a vacuum of 0.01 mmHg. 1.694 g (Yd=85%) of a colorless oil were isolated. The spectroscopic characteristics are as follows:

| | |
|---|---|
| $^1$H NMR(CDCl$_3$, δ ppm/TMS): | 1.22(d, 6H, $^3J_{HH}$=6.6Hz, C$\underline{H}_3$ iPr) |
| | 1.38(d, 6H, $^3J_{HH}$=6.6Hz, C$\underline{H}_3$ iPr) |
| | 2.44(s, 3H, CH$_3$ tolyl) |
| | 3.45(hept, 1H, $^3J_{HH}$= 6.6Hz, C$\underline{H}$ iPr) |
| | 4.33(hept, 1H, $^3J_{HH}$= 6.6Hz, C$\underline{H}$ iPr) |
| | 7.23(d, 2H, $^3J_{HH}$=7.8Hz, C$\underline{H}$ aryl) |
| | 7.45(d, 2H, $^3J_{HH}$=7.8Hz, C$\underline{H}$ aryl) |
| $^{13}$C NMR(CDCl$_3$, δ ppm/TMS): | 21.9(s, 1C, $\underline{C}H_3$ tolyl) |
| | 22.7(s, 2C, $\underline{C}H_3$ iPr) |
| | 27.6(s, 2C, $\underline{C}H_3$ iPr) |
| | 45.0(s, 1C, $\underline{C}H$ iPr) |
| | 49.7(s, 1C, $\underline{C}H$ iPr) |
| | 128.8(s, 2C, $\underline{C}H$ aryl) |
| | 133.6(s, 2C, $\underline{C}H$ aryl) |
| | 137.8(s, 1C, $\underline{C}^{IV}$—CH$_3$ aryl) |
| $^{11}$B NMR(CDCl$_3$, δ ppm/Et$_2$O.BF$_3$): | 37.8(d, $^1J_{BH}$=80.5Hz, $\underline{B}$H) |
| Infrared: | 2477 and 2443 cm$^{-1}$($ν_{BH}$) |
| Mass spectrometry: | calculated for $[C_{13}H_{22}BN]^+$: 203.18453 |
| | found(e.i.): 203.1845(0.2 ppm) |

EXAMPLE 2

Various aryl(diisopropylamino)boranes were prepared from diisopropylamine-borane obtained in accordance with the procedure described in Example 1, according to the following process:

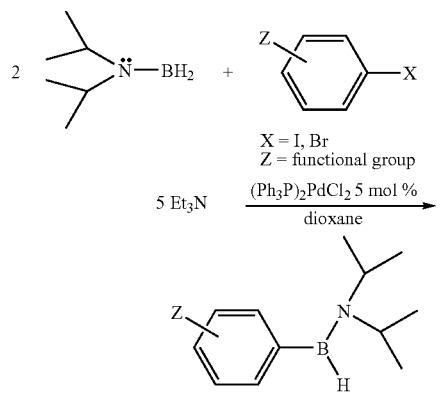

One equivalent of palladium catalyst $(Ph_3P)_2PdCl_2$, 20 equivalents of aryl halide, 100 equivalents of triethylamine, 700 equivalents of dioxane and 40 equivalents of diisopropylaminoborane are introduced into a 250 ml Schlenk vessel dried beforehand under argon. The Schlenk vessel is subsequently equipped with a reflux condenser connected at the top to a bubbler. The reaction mixture is stirred magnetically and is heated at 70° C. for 15 h. The reaction mixture is subsequently allowed to return, under argon, to ambient temperature. The solvent and the excess reactants are evaporated under the vacuum of a vane pump. The residue obtained is taken up in anhydrous ether and is then filtered under argon through dry Celite® 545. The filtrate is again evaporated and the residue is distilled in a Kügelrohr distillation apparatus under the vacuum of a vane pump. The product obtained from various halides and the yield of the product isolated are shown in the following table.

| Aryl halide | X | Arylaminoborane | Yd (isolated) |
|---|---|---|---|
| phenyl-X | I / Br | phenyl-B(H)(NiPr2) | 100% / 75% |
| 4-methylphenyl-X | I / Br | 4-methylphenyl-B(H)(NiPr2) | 85% / 80% |
| 3-methylphenyl-X | I / Br | 3-methylphenyl-B(H)(NiPr2) | 91% / 73% |
| 2-methylphenyl-X | I / Br | 2-methylphenyl-B(H)(NiPr2) | 94% / 50% |
| 4-methoxyphenyl-X | I / Br | 4-methoxyphenyl-B(H)(NiPr2) | 100% / 93% |
| 2-methoxyphenyl-X | I / Br | 2-methoxyphenyl-B(H)(NiPr2) | 86% / 87% |
| 4-(methylthio)phenyl-X | Br | 4-(methylthio)phenyl-B(H)(NiPr2) | 90% |
| 1-naphthyl-X | I / Br | 1-naphthyl-B(H)(NiPr2) | 80% / 25% |
| 2-thienyl-X | I | 2-thienyl-B(H)(NiPr2) | 99% |
| 4-(dimethylamino)phenyl-X | I | 4-(dimethylamino)phenyl-B(H)(NiPr2) | 95% |

EXAMPLE 3

(p-methoxyphenyl)(N,N-dicyclohexylamino)borane

Preparation of the N,N-dicyclohexylamine-borane Complex

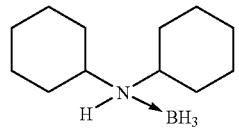

The N,N-dicyclohexylamine-borane complex was prepared by a process analagous to that of Example 1 using N,N-dicyclohexylamine instead of diisopropylamine. 9.52 g of the dicyclohexylamine-borane complex were obtained in the form of a white solid (yield: 97%). The spectroscopic characteristics of the compound are given below.

$^1$H NMR(CDCl$_3$, δ ppm/TMS): 1.00–1.50(m, 4H, C$\underline{H}_2$cyclohexyl)
1.50–2.05(m, 16H, C$\underline{H}_2$ cyclohexyl)
2.70–3.05(m, 2H, C$\underline{H}_2$ cyclohexyl)

| $^{13}$C NMR(CDCl$_3$, δ ppm/TMS): | 25.7(s, 2C, CH$_2$ cyclohexyl) |
| | 25.8(s, 2C, CH$_2$ cyclohexyl) |
| | 26.1(s, 2C, CH$_2$ cyclohexyl) |
| | 30.0(s, 2C, CH$_2$ cyclohexyl) |
| | 31.3(s, 2C, CH$_2$ cyclohexyl) |
| | 61.0(s, 2C, CH cyclohexyl) |
| $^{11}$B NMR(CDCl$_3$, δ ppm/Et$_2$O.BF$_3$): | −20.5(q, 1B, $^1$J$_{BH}$ = 83Hz, BH$_3$) |
| IR: | 2305 and 2409 cm$^{-1}$(ν$_{BH}$). |

Preparation of N,N-dicyclohexylaminoborane

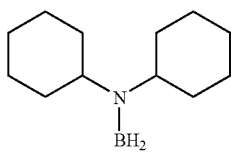

N,N-Dicyclohexylaminoborane was prepared by a process analogous to that of Example 1 using the N,N-dicyclohexylamine-borane complex instead of the diisopropylamine-borane complex. The N,N-dicyclohexylaminoborane distills at the column top at approximately 129° C. under 0.01 mmHg. 3.644 g (18.9 mmol) of compound are recovered in the form of a colorless oil, corresponding to a yield of 79%.

Spectroscopic Characteristics:

| $^1$H NMR(CDCl$_3$, δ ppm/TMS): | 1.00–2.00(m, 20H, CH$_2$ cyclohexyl) |
| | 2.75–3.00(m, 2H, CH cyclohexyl) |
| $^{13}$C NMR(CDCl$_3$, δ ppm/TMS): | 25.7(s, 2C, CH$_2$ cyclohexyl) |
| | 26.5(s, 4C, CH$_2$ cyclohexyl) |
| | 36.0(s, 4C, CH$_2$ cyclohexyl) |
| | 62.1(s, 2C, quater. C cyclohexyl) |
| $^{11}$B NMR(CDCl$_3$, δ ppm/Et$_2$O.BF$_3$): | 35.2(t, BH$_2$, $^1$J$_{BH}$=118Hz) |
| Mass Spectrometry: | calculated for C$_{12}$H$_{24}$BN]$^{•+}$: 193.2018 |
| | found(e.i.): 193.1961(20 ppm) |
| IR: | 2438, 2461 and 2527 cm$^{-1}$(ν$_{BH}$). |

Preparation of (p-methoxyphenyl) (dicyclohexylamino)borane

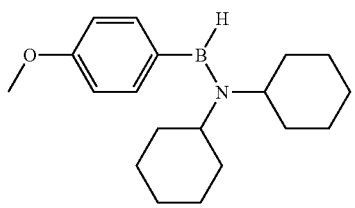

1.130 g (0.19 mmol) of palladium catalyst (Ph$_3$P)$_2$PdCl$_2$, 0.868 g (3.7 mmol) of p-iodotoluene, 2.5 ml (18.5 mmol) of triethylamine, 15 ml of dioxane and 0.708 g (3.7 mmol) of dicyclohexylaminoborane were introduced into a 100 ml Schlenk vessel dried beforehand under argon. The Schlenk vessel was subsequently equipped with a reflux condenser connected via the top to a bubbler. The reaction mixture was stirred magnetically and heated at 70° C. for 15 h. The reaction mixture was subsequently allowed to return, under argon, to ambient temperature. The solvent and the excess reactants were evaporated under the vacuum of a vane pump. The residue obtained was taken up in anhydrous ether and then filtered under argon through dry Celite® 545. The filtrate was again evaporated and the residue was distilled in a Kügelrohr distillation apparatus (T=40° C.) under a vacuum of 0.01 mmHg. 0.884 g (Yd=81%) of a white solid was isolated. The spectroscopic characteristics are as follows:

| $^1$H NMR(CDCl$_3$, δ ppm/TMS): | 1.25(m, 4H, CH$_2$, cyclohexyl) |
| | 1.70(m, 16H, CH$_2$, cyclohexyl) |
| | 2.90(m, 2H, CH cyclohexyl) |
| | 3.87(s, 3H, CH$_3$ anisyl) |
| | 6.96(d, 2H, $^3$J$_{HH}$=8.56 Hz, CH aryl) |
| | 7.46(d, 2H, $^3$J$_{HH}$=8.56 Hz, CH aryl) |
| $^{13}$C NMR(CDCl$_3$, δ ppm/TMS): | 25.7(s, CH$_2$ cyclohexyl) |
| | 25.8(s, CH$_2$ cyclohexyl) |
| | 25.9(s, 2C, CH$_2$ cyclohexyl) |
| | 26.8(s, 2C, CH$_2$ cyclohexyl) |
| | 32.9(s, 2C, CH$_2$ cyclohexyl) |
| | 37.7(s, 2C, CH$_2$ cyclohexyl) |
| | 55.0(s, CH$_3$ anisyl) |
| | 55.1(s, CH cyclohexyl) |
| | 58.2(s, CH cyclohexyl) |
| | 113.2(s, 2C, CH aryl) |
| | 135.5(s, 2C, CH aryl) |
| | 159.5(s, C$^{IV}$—OCH$_3$ aryl) |
| $^{11}$B NMR(CDCl$_3$, δ ppm/Et$_2$O.BF$_3$): | 38.1(s, ν$_{1/2}$=577.8Hz, BH) |
| Infrared: | 2433 and 2477 cm$^{-1}$ (ν$_{BH}$) |
| Mass spectrometry: | calculated for C$_{19}$H$_{30}$BNO]$^+$: 299.24205 |
| | found(e.i.): 299.24294(2 ppm) |

EXAMPLE 4

(p-methoxyphenyl)(2,2,6,6-tetramethylpiperidino)borane

Preparation of the 2,2,6,6-tetramethylpiperidine-borane Complex

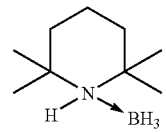

The 2,2,6,6-tetramethylpiperidine-borane complex was prepared by a process analogous to that of Example 1 using 2,2,6,6-tetramethylpiperidine instead of diisopropylamine. 9.41 g of the 2,2,6,6-tetramethylpiperidine-borane complex were obtained in the form of a white solid (quantitative yield). The spectroscopic characteristics of the compound are given below.

| $^1$H NMR(CDCl$_3$, δ ppm/TMS): | 1.38(s, 6H, CH$_3$) |
| | 1.44(s, 6H, CH$_3$) |
| | 1.50–1.80(m, 6H, CH$_2$) |
| $^{13}$C NMR(CDCl$_3$, δ ppm/TMS): | 17.0(s, 1C, CH$_2$) |
| | 21.0(s, 2C, CH$_3$) |
| | 34.3(s, 2C, CH$_3$) |
| | 41.3(s, 1C, CH$_2$) |
| | 59.0(s, 2C, quaternary C) |
| $^{11}$B NMR(CDCl$_3$, δ ppm/Et$_2$O.BF$_3$): | −22.2(q, 1B, $^1$J$_{BH}$=96Hz, BH$_3$). |

Preparation of 2,2,6,6-tetramethylpiperidino-1-borane

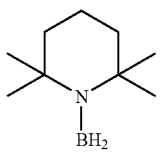

2,2,6,6-Tetramethylpiperidino-1-borane was prepared by a process analogous to that of Example 1 using the 2,2,6,6-tetramethylpiperidino-1-borane complex instead of the diisopropylamine-borane complex. The 2,2,6,6-tetramethylpiperidino-1-borane distills at the column top at 50° C. under 0.01 mmHg. 1.842 g (12.1 mmol) of a colorless oil were recovered, corresponding to a yield of 81%.

Spectroscopic Characteristics:

| | |
|---|---|
| $^1$H NMR(CDCl$_3$, δ ppm/TMS): | 1.25(s, 12H, C$\underline{H}_3$) |
| | 1.40–1.70(m, 6H, C$\underline{H}_2$) |
| $^{13}$C NMR(CDCl$_3$, δ ppm/TMS): | 15.7(s, 2C, $\underline{C}H_2$) |
| | 34.0(s, 4C, $\underline{C}H_3$) |
| | 37.8(s, 2C, $\underline{C}H_2$) |
| | 54.2(s, 1C, $\underline{C}^{IV}$) |
| $^{11}$B NMR(CDCl$_3$, δ ppm/Et$_2$O.BF$_3$): | δ=35.7(t, 1B, $^1J_{BH}$=127Hz, $\underline{B}H_2$) |
| Mass spectrometry: [M-CH$_3^\bullet$] | calculated for: C$_8$H$_{17}$BN]$^+$: 138.1454 |
| | found(e.i.): 138.1432(16 ppm) |
| IR: | 2488, 2519 and 2564 cm$^{-1}$(ν$_{BH}$). |

Preparation of (p-methoxyphenyl)(2,2,6,6-tetramethyl-piperidino)borane

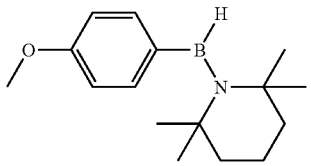

The above borane was prepared by a process analogous to that of Example 3 using (2,2,6,6-tetramethylpiperidino)borane instead of dicyclohexylaminoborane. 1.562 g of a colorless oil were isolated, which oil distills at 90° C. under 0.01 mmHg. The spectroscopic characteristics are as follows:

| | |
|---|---|
| $^1$H NMR(CDCl$_3$, δ ppm/TMS): | 1.44(broad s, 12H, C$\underline{H}_3$ piperidine) |
| | 1.76(m, 6H, C$\underline{H}_2$ piperidine) |
| | 3.87(s, 3H, O—C$\underline{H}_3$) |
| | 6.95(d, 2H, $^3J_{HH}$=8.45Hz, C$\underline{H}$ aryl) |
| | 7.37(d, 2H, $^3J_{HH}$=8.45Hz, C$\underline{H}$ aryl) |
| $^{13}$C NMR(CDCl$_3$, δ ppm/TMS): | 15.7(s, 1C, $\underline{C}H_2$ piperidine) |
| | 35.0(s, 4C, $\underline{C}H_3$ piperidine) |
| | 37.4(s, 2C, $\underline{C}H_2$ piperidine) |
| | 55.0(s, 1C, O—$\underline{C}H_3$) |
| | 56.1(s, 2C, $\underline{C}^{IV}$piperidine) |
| | 113.0(s, 2C, $\underline{C}H$ aryl) |
| | 132.0(s, 2C, $\underline{C}H$ aryl) |
| | 158.3(s, 1C, $\underline{C}^{IV}$—OMe aryl) |
| $^{11}$B NMR(CDCl$_3$, δ ppm/Et$_2$O.BF$_3$): | 41.5(broad s, 1B, ν$_{1/2}$=491.1Hz, $\underline{B}$H) |
| Mass spectrometry: | [M-CH$_3^\bullet$] calculated for C$_{15}$H$_{23}$BNO]$^+$: 244.18727 |
| | found(e.i.): 244.18764(1 ppm) |
| Infrared: | 2414 and 2468 cm$^{-1}$(ν$_{BH}$) |

EXAMPLE 5

(p-methoxyphenyl)[(methylbenzyl)(isopropyl)amino]borane

Preparation of the [(methylbenzyl)(isopropyl)amine]-borane Complex

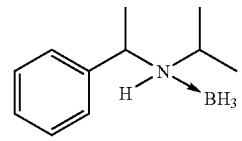

The (methylbenzyl)(isopropyl)amine-borane complex was prepared by a process analogous to that of Example 1 using (methylbenzyl)(isopropyl) amine instead of diisopropylamine. 16.33 g of the (methylbenzyl)(isopropyl)amine-borane complex were obtained in the form of a white solid (quantitative yield). The spectroscopic characteristics of the compound are given below.

| | |
|---|---|
| $^1$H NMR(CDCl$_3$, δ ppm/TMS): | 1.18(d, 3H, C$\underline{H}_3$ isopropyl, $^3J_{HH}$=6.7Hz) |
| | 1.24(d, 3H, $^3J_{HH}$=6.7Hz, C$\underline{H}_3$ isopropyl) |
| | 1.71(d, 3H, $^3J_{HH}$=6.8Hz, Ph—CH—C$\underline{H}_3$) |
| | 2.99(hept d, 1H, $^3J_{HH}$=6.7Hz, C$\underline{H}$ isopropyl) |
| | 3.41(broad s, 1H, N—$\underline{H}$) |
| | 3.96(q, 1H, $^3J_{HH}$=6.8Hz, CH benzyl) |
| | 7.39–7.61(m, 5H, C$\underline{H}$ aryl) |
| $^{13}$C NMR(CDCl$_3$, δ ppm/TMS): | 14.0(s, 1C, Ar—CH—$\underline{C}H_3$) |
| | 20.3(s, 1C, $\underline{C}H_3$ isopropyl) |
| | 20.5(s, 1C, $\underline{C}H_3$ isopropyl) |
| | 50.5(s, 1C, $\underline{C}H$ benzyl) |
| | 61.3(s, 1C, $\underline{C}H$ isopropyl) |
| | 125.4(s, 2C, $\underline{C}H$ aryl) |
| | 127.4(s, 1C, $\underline{C}H$ aryl) |
| | 128.3(s, 2C, $\underline{C}H$ aryl) |
| | 140.4(s, 1C, $\underline{C}^{IV}$ aryl) |
| $^{11}$B NMR(CDCl$_3$, δ ppm/Et$_2$O.BF$_3$): | −21.0(q, 1B, $^1J_{BH}$=90Hz, $\underline{B}H_3$). |

Preparation of [(methylbenzyl)(isopropyl)amino]borane

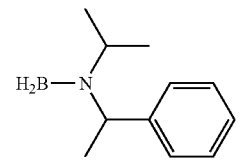

[(Methylbenzyl)(isopropyl)amino]borane was prepared by a process analogous to that of Example 1 using the (methylbenzyl)(isopropyl)amine-borane complex instead of the diisopropylamine-borane complex. The [(methylbenzyl)(iso-propyl)]aminoborane distills at the column top at approximately 74° C. under 0.01 mmHg. 1.99 g (11.4 mmol) of a colorless oil are recovered, corresponding to a yield of 94%.

Spectroscopic Characteristics:

| $^1$H NMR(CDCl$_3$, δ ppm/TMS): | 1.13(d, 3H, $^3J_{HH}$=6.7Hz, C$\underline{H}_3$ isopropyl)<br>1.28(d, 3H, $^3J_{HH}$=6.7Hz, C$\underline{H}_3$ isopropyl)<br>1.68(d, 3H, $^3J_{HH}$=7Hz, Ar—CH—C$\underline{H}_3$)<br>3.26(hept, 1H, $^3J_{HH}$=6.7Hz, C$\underline{H}$ isopropyl)<br>4.64(q, 1H, $^3J_{HH}$=7Hz,<br>Ar—C$\underline{H}$—CH$_3$)<br>7.40(m, 5H, C$\underline{H}$ aryl) |
|---|---|
| $^{13}$C NMR(CDCl$_3$, δ ppm/TMS): | 23.7(s, 1C, Ar—CH—$\underline{C}$H$_3$)<br>25.8(s, 1C, $\underline{C}$H$_3$ isopropyl)<br>26.2(s, 1C, $\underline{C}$H$_3$ isopropyl)<br>52.0(s, 1C, $\underline{C}$H isopropyl)<br>62.8(s, 1C, Ar—$\underline{C}$H—CH$_3$)<br>127.4(s, C, $\underline{C}$H aryl)<br>127.5(s, 2C, $\underline{C}$H aryl)<br>128.7(s, 1C, $\underline{C}$H aryl)<br>144.6(s, 1C, $\underline{C}^{IV}$ aryl) |
| $^{11}$B NMR(CDCl$_3$, δ ppm/Et$_2$O.BF$_3$): | 35.8(t, 1B, $^1J_{BH}$=114.9Hz, $\underline{B}$H$_2$) |
| Mass spectrometry: | calculated for C$_{11}$H$_{18}$BN]$^{+ \cdot}$:<br>175.15323<br>found(e.i.): 175.1493(22 ppm) |
| Infrared: | 2461, 2496 and 2542 cm$^{-1}$(ν$_{BH}$). |

Preparation of (p-methoxyphenyl)[(methylbenzyl)-(isopropyl)amino]borane

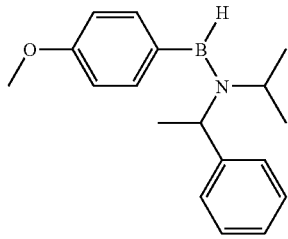

The above borane was prepared by a process analogous to that of Example 3 using [(methylbenzyl)(isopropyl)amino]-borane instead of dicyclohexylaminoborane. 1.546 g (Yd=51%) of a colorless oil were isolated by distillation at 125° C. under a pressure of 0.01 mmHg. The spectroscopic characteristics are as follows:

| $^1$H NMR(CDCl$_3$, δ ppm/TMS): | 1.06(d, 3H, $^3J_{HH}$=6.63 Hz, C$\underline{H}_3$ isopropyl)<br>1.42(d, 3H, $^3J_{HH}$=6.63 Hz, C$\underline{H}_3$ isopropyl)<br>1.74(d, 3H, $^3J_{HH}$=6.99 Hz,<br>Ph—CH—C$\underline{H}_3$)<br>3.18(hept, 1H, $^3J_{HH}$=6.63Hz, C$\underline{H}$ isopropyl)<br>3.92(s, 3H, O—C$\underline{H}_3$)<br>5.50(q, 1H, $^3J_{HH}$=6.99HZ,<br>Ph—C$\underline{H}$—CH$_3$)<br>7.05(d, 2H, $^3J_{HH}$=8.70Hz, C$\underline{H}$ aryl)<br>7.42(m, 5H, C$\underline{H}$ phenyl)<br>7.67(d, 2H, $^3J_{HH}$=8.70Hz, C$\underline{H}$ aryl) |
|---|---|
| $^{13}$C NMR(CDCl$_3$, δ ppm/TMS): | 19.2(s, 1C, Ph—CH—$\underline{C}$H$_3$)<br>26.0(s, 1C, $\underline{C}$H$_3$ isopropyl)<br>28.0(s, 1C, $\underline{C}$H$_3$ isopropyl)<br>47.0(s, 1C, $\underline{C}$H isopropyl)<br>55.1(s, 1C, O—$\underline{C}$H$_3$)<br>55.9(s, 1C, Ph—$\underline{C}$H—CH$_3$)<br>113.6(s, 2C, $\underline{C}$H aryl)<br>127.1(s, 2C, $\underline{C}$H phenyl)<br>127.9(s, 2C, $\underline{C}$H phenyl)<br>128.7(s, 1C, $\underline{C}$H phenyl)<br>135.4(s, 2C, $\underline{C}$H aryl)<br>142.5(s, 1C, $\underline{C}^{IV}$ phenyl)<br>160.1(s, 1C, $\underline{C}^{IV}$—OMe aryl) |
| $^{11}$B NMR(CDCl$_3$, δ ppm/Et$_2$O.BF$_3$): | 39.2(broad S, 1B, V$_{1/2}$=674.0Hz, $\underline{B}$H) |
| Infrared: | 2414 and 2464 cm$^{-1}$(ν$_{Bh}$) |
| Mass spectrometry: | calculated for C$_{18}$H$_{24}$NOB]$^+$:<br>281.19509<br>found(e.i.): 281.19474(1 ppm). |

What is claimed is:

1. A compound corresponding to the formula A-BH—NR$^1$R$^2$, in which:
   R$^1$ and R$^2$ are identical or different groups chosen from linear alkyl groups, branched alkyl groups, cyclic alkyl groups or arylalkyl groups, or else the R$^1$ and R$^2$ groups together form an alkylene group, and
   A represents:
   a) an optionally polycondensed aromatic group optionally carrying at least one substituent,
   b) an optionally polycondensed heteroaromatic group optionally carrying at least one substituent,
   c) a group chosen from vinyl, dienyl, polyenyl or alkynyl groups optionally carrying at least one substituent,
   said optional substituents of the groups defined in a), b) and c) being chosen from alkyls, alkoxys, aminos, dialkylaminos, halogens, nitrile groups, ester groups, amide groups, aldehyde groups protected in the acetal or thioacetal form, ketone groups protected in the acetal or thioacetal form, trialkylsilyl groups and dialkoxyboryl groups,
   with the proviso that A is different from a fluorenyl group when R$^1$ and R$^2$ together form an alkylene group, and A is different from a phenyl group when R$^1$ and R$^2$ each are an ethyl.

2. The compound as claimed in claim 1, wherein the R$^1$ or R$^2$ substituent is chosen from linear alkyls having from 2 to 20 carbon atoms, branched alkyls having from 3 to 20 carbon atoms or cycloalkyls having from 3 to 20 carbon atoms.

3. The compound as claimed in claim 1, wherein the R$^1$ and R$^2$ substituents are chiral groups.

4. The compound as claimed in claim 1, wherein the R$^1$ or R$^2$ substituent is an R$^8$-Ph-CH(R$^3$) group in which Ph represents a phenyl group, R$^8$ represents H or a substituent chosen from halogens, alkyls, alkoxys, alkylthios, ketone groups protected in the acetal or thioacetal form, and trialkylsilyl groups, and R$^3$ is an alkyl group having from 1 to 20 carbon atoms.

5. The compound as claimed in claim 1, wherein the A substituent is a phenyl, a tolyl or a methoxyphenyl.

6. The compound as claimed in claim 1, wherein R$^1$ and R$^2$ form an alkylene group corresponding to the formula —CR$^4$R$^5$—(CH$_2$)$_n$—CR$^6$R$^7$— in which $3 \leq n \leq 5$ and the R$^4$ to R$^7$ substituents are chosen, independently of one another, from H and alkyl radicals having from 1 to 20 carbon atoms.

7. The compound as claimed in claim 6, wherein the alkylene group is 1,1,5,5-tetramethylpentylene.

8. A process for the preparation of a compound corresponding to the formula A-BH—NR$^1$R$^2$in which:
   R$_1$ and R$_2$ are identical or different groups chosen from linear alkyl groups, branched alkyl groups, cyclic alkyl groups or arylalkyl groups, or else the R and $R_2$ groups together form an alkylene group, and A represents:
  a) an optionally polycondensed aromatic group optionally carrying at least one substituent,
  b) an optionally polycondensed heteroaromatic group optionally carrying at least one substituent.
  c) a group chosen from vinyl, dienyl, polyenyl or alkynyl groups optionally carrying at least one substituent.

said optional substituents of the groups defined in a), b) and c) being chosen from alkyls, alkoxys, aminos, dialkylaminos, halogens, nitrile groups, ester groups, amide groups, aldehyde groups protected in the acetal or thioacetal form, ketone groups protected in the acetal or thioacetal form, trialkylsilyl groups and dialkoxyboryl groups, said process comprising two stages, in which:

during the first stage, an amine-borane complex $R_1R^2NH.BH_3$ is prepared and is then converted to aminoborane $R^1R^2NBH_2$ by heating; and
  during the second stage, the aminoborane $R^1R^2NBH_2$ is reacted with a compound A-X, in which X is a leaving group, in the presence of a catalytic amount of a complex of a transition metal and of a base, in an aprotic organic solvent or a base, and then the excess reactants and solvent are removed under vacuum.

9. The process as claimed in claim 8, wherein, to prepare the amine-borane complex during the first stage, an amine $R^1R^2NH$ is reacted under an inert atmosphere with a borane source in a polar aprotic solvent at a temperature of less than 50° C. and then the solvent is removed under vacuum.

10. The process as claimed in claim 9, wherein the borane source is a commercial complex, selected from $Me_2S.BH_3$ or $THF.BH_3$.

11. The process as claimed in claim 9, wherein the polar aprotic solvent used in the first stage is chosen from ethers.

12. The process as claimed in claim 11, wherein the polar aprotic solvent is THF, dioxane, DME or diglyme, or tert-butyl methyl ether (TBDME).

13. The process as claimed in claim 8, wherein, during the first stage, the amine-borane complex is prepared by reaction of the hydrochloride of the amine $R^1R^2NH.HCl$ with $NaBH_4$ or $KBH_4$ and then the amine-borane complex $R^1R^2NH.BH_3$ is isolated by filtration and removal of the solvent.

14. The process as claimed in claim 8, wherein the aminoborane $R^1R^2NBH_2$ obtained by heating the amine-borane complex is recovered by distillation.

15. The process as claimed in claim 8, wherein the organic solvent of the second stage is chosen from ethers, amines and aromatic hydrocarbons.

16. The process as claimed in claim 8, wherein the base introduced into the reaction medium during the second stage of the process is chosen from cyclic or linear trialkylamines, cyclic or linear secondary amines, or aromatic amines of the pyridine or quinoline type.

17. The process as claimed in claim 8, wherein the complex of a transition metal is a palladium compound stabilized by a ligand.

18. The process as claimed in claim 17, wherein the palladium compound is chosen from $PdCl_2$, palladium diacetylacetonate $Pd(acac)_2$, palladium acetate $Pd(OAc)_2$, palladium cyanide $Pd(CN)_2$ or allylpalladium chloride $(CH_2=CHCH_2PdCl)_2$.

19. The process as claimed in claim 17, wherein the ligand is a phosphine, an arsine, an aromatic or nonaromatic nitrile, an isonitrile, an aromatic or heteroaromatic imine, or an imidazo-2-ylidene.

20. The process as claimed in claim 8, wherein the leaving group is a halogen atom or a triflate, tosylate, mesylate, diazonium or phosphate group.

21. A process for the preparation of an arylboratrane, which comprises reacting an arylborane with a dihydroxyethylamine, said arylborane corresponding to the formula A-BH—$NR^1R^2$, in which:
  $R^1$ and $R^2$ are identical or different groups chosen from linear alkyl groups, branched alkyl groups, cyclic alkyl groups or arylalkyl groups, or else the $R^1$ and $R^2$ groups together form an alkylene group, and
  A represents:
    a) an optionally polycondensed aromatic group optionally carrying at least one substituent,
    b) an optionally polycondensed heteroaromatic group optionally carrying at least one substituent,
    c) a group chosen from vinyl, dienyl, polyenyl or alkynyl groups optionally carrying at least one substituent, said optional substituents of the groups defined in a), b) and c) being chosen from alkyls, alkoxys, aminos, dialkylaminos, halogens, nitrile groups, ester groups, amide groups, aldehyde groups protected in the acetal or thioacetal form, ketone groups protected in the acetal or thioacetal form, trialkylsilyl groups and dialkoxyboryl groups.

22. A process for the preparation of a 2-aryl-5,5-dimethyl-1,3,2-dioxaborinane, which comprises reacting an arylborane with 2,2-dimethylpropane-1,4-diol, said arylborane corresponding to the formula A-BH—$NR^1R^2$, in which:
  $R^1$ and $R^2$ are identical or different groups chosen from linear alkyl groups, branched alkyl groups, cyclic alkyl groups or arylalkyl groups, or else the $R^1$ and $R^2$ groups together form an alkylene group, and
  A represents:
    a) an optionally polycondensed aromatic group optionally carrying at least one substituent,
    b) an optionally polycondensed heteroaromatic group optionally carrying at least one substituent,
    c) a group chosen from vinyl, dienyl, polyenyl or alkynyl groups optionally carrying at least one substituent, said optional substituents of the groups defined in a), b) and c) being chosen from alkyls, alkoxys, aminos, dialkylaminos, halogens, nitrile groups, ester groups, amide groups, aldehyde groups protected in the acetal or thioacetal form, ketone groups protected in the acetal or thioacetal form, trialkylsilyl groups and dialkoxyboryl groups.

23. A process for the preparation of an arylboronic acid, which comprises reacting an arylborane with excess methanol, in order to obtain an aryldimethoxyborane, and then hydrolyzing the aryldimethoxyborane, said arylborane corresponding to the formula A-BH—$NR^1R^2$, in which:
  $R^1$ and $R^2$ are identical or different groups chosen from linear alkyl groups, branched alkyl groups, cyclic alkyl groups or arylalkyl groups, or else the $R^1$ and $R^2$ groups together form an alkylene group, and
  A represents:
    a) an optionally polycondensed aromatic group optionally carrying at least one substituent,
    b) an optionally polycondensed heteroaromatic group optionally carrying at least one substituent,
    c) a group chosen from vinyl, dienyl, polyenyl or alkynyl groups optionally carrying at least one substituent, said optional substituents of the groups defined in a), b) and c) being chosen from alkyls, alkoxys, aminos, dialkylaminos, halogens, nitrile groups, ester groups, amide groups, aldehyde groups protected in the acetal or thioacetal form, ketone groups protected in the acetal or thioacetal form, trialkylsilyl groups and dialkoxyboryl groups.

24. A process for the preparation of a (B,B-diaryl)aminoborane compound, which comprises reacting an arylborane with a compound A-X in the presence of a Pd(0) catalyst and base said arylborane corresponding to the formula A-BH—$NR^1R^2$, in which:

$R^1$ and $R^2$ are identical or different groups chosen from linear alkyl groups, branched alkyl groups, cyclic alkyl groups or arylalkyl groups, or else the $R^1$ and $R^2$ groups together form an alkylene group, and A represents:
  a) an optionally polycondensed aromatic group optionally carrying at least one substituent,
  b) an optionally polycondensed heteroaromatic group optionally carrying at least one substituent,
  c) a group chosen from vinyl, dienyl, polyenyl or alkynyl groups optionally carrying at least one substituent, said optional substituents of the groups defined in a), b) and c) being chosen from alkyls, alkoxys, aminos, dialkylaminos, halogens, nitrile groups, ester groups, amide groups, aldehyde groups protected in the acetal or thioacetal form, ketone groups protected in the acetal or thioacetal form, trialkylsilyl groups and dialkoxyboryl groups.

25. A process for the preparation of a compound A-A, which comprises reacting an arylborane with a compound A-Z in the presence of a Pd(O) catalyst, a base and water, said arylborane corresponding to the formula A-BH—$NR^1R^2$, in which:

$R^1$ and $R^2$ are identical or different groups chosen from linear alkyl groups, branched alkyl groups, cyclic alkyl groups or arylalkyl groups, or else the $R^1$ and $R^2$ groups together form an alkylene group, and A represents:
  a) an optionally polycondensed aromatic group optionally carrying at least one substituent,
  b) an optionally polycondensed heteroaromatic group optionally carrying at least one substituent,
  c) a group chosen from vinyl, dienyl, polyenyl or alkynyl groups optionally carrying at least one substituent, said optional substituents of the groups defined in a), b) and c) being chosen from alkyls, alkoxys, aminos, dialkylaminos, halogens, nitrile groups, ester groups, amide groups, aldehyde groups protected in the acetal or thioacetal form, ketone groups protected in the acetal or thioacetal form, trialkylsilyl groups and dialkoxyboryl groups.

* * * * *